United States Patent [19]
Christensen

[11] Patent Number: 5,885,516
[45] Date of Patent: Mar. 23, 1999

[54] METHOD AND A SYSTEM FOR MANUFACTURING BROAD AIRLAID PAPER WEBS CONTAINING AN ABSORBING POWDER

[75] Inventor: John Harly Mosgaard Christensen, Risskov, Denmark

[73] Assignee: Scan-Web I/S, Risskov, Denmark

[21] Appl. No.: 793,974
[22] PCT Filed: Sep. 6, 1995
[86] PCT No.: PCT/DK95/00357
§ 371 Date: May 27, 1997
§ 102(e) Date: May 27, 1997
[87] PCT Pub. No.: WO96/07792
PCT Pub. Date: Mar. 14, 1996

[30] Foreign Application Priority Data

Sep. 6, 1994 [DK] Denmark .................................. 1026/94

[51] Int. Cl.[6] .............................. B27N 3/04; D21H 27/42
[52] U.S. Cl. ......................... 264/518; 264/510; 264/113; 425/81.1; 425/83.1
[58] Field of Search .................................... 264/113, 518, 264/510; 425/81.1, 83.1

[56] References Cited

U.S. PATENT DOCUMENTS

| 4,908,175 | 3/1990 | Angstadt ................................. 264/113 |
| 4,927,582 | 5/1990 | Bryson ................................... 264/113 |
| 5,429,788 | 7/1995 | Ribble et al. ........................... 264/510 |
| 5,445,777 | 8/1995 | Noel et al. .............................. 264/113 |
| 5,558,832 | 9/1996 | Noel et al. .............................. 264/510 |

FOREIGN PATENT DOCUMENTS 0 168 957 1/1986 European Pat. Off. .
0 520 798 12/1992 European Pat. Off. .

*Primary Examiner*—Mary Lynn Theisen
*Attorney, Agent, or Firm*—Browdy and Neimark

[57] ABSTRACT

Method and apparatus of forming an air laid paper web. Superabsorbing powder is introduced at an intermediate stage between the initial supply of the fibers to the air laying unit and the final formation of the web. A first coarse distribution of the powder is effected in a compulsory manner, independently of the initial supply of fiber material while the final distribution of powder is effected by means of the same air flows which cause the final distribution of the fiber material for forming the even web layer. In this manner the powder is effectively mixed evenly into the fiber material.

7 Claims, 3 Drawing Sheets

METHOD AND A SYSTEM FOR MANUFACTURING BROAD AIRLAID PAPER WEBS CONTAINING AN ABSORBING POWDER

The present invention relates to the production of air-laid paper webs containing a liquid super absorbing powder. The basic material in such webs is cellulose fibres, though normally with a certain content of heat activated synthetic fibres for bonding of the laid out web, and it is well known that such a fibrous material may also contain super absorbing fibres evenly distributed in the web.

However, in particular for economical reasons it is desirable to use the said powder, also known as SAP, instead of the absorbing fibres, but it is much more difficult to achieve a reasonably homogenous admixture of the SAP in the web material.

It is well known that with different prior art laying techniques it is possible to produce an absorbing web material on a moved wire passing a first distributor head for laying out a bottom web layer on the wire, then passing a powder dispenser laying out a SAP layer on the bottom web layer, and then passing another distributor head operating to lay out an upper top web layer. However, the SAP particles are not really bonded in the web material, which dusts heavily during the further processing, whilst also the final absorbing products exhibit strong tendencies to delamination.

On this background it is also known that instead it should be endeavoured to mix the SAP material into the fibre material, and to this end it has been a natural measure to add the powder to the flow of the air fluidised fibre material supplied to the distributor head, normally from a hammer mill in which a dry pulp material is desintegrated. This may result in an efficient admixing due to high turbulence in the air, but it has nevertheless been necessary to accept a noticeable inhomogeneity in the final product, all according to the applied airlaying technique. Thus, by a concentrated supply of the fibre/SAP/air flow down into a distributor head having means for agitating and distributing of the material over a classification screen above the forming wire, there may be found a higher SAP concentration underneath the flow supply area than at the periphery; in the web product, this gives rise to a formation of stripes with mutually different SAP concentrations, and if the SAP is dosed at such high rate that a desired concentration is obtained in the peripheral areas, then dusting may occur from the more concentrated zone or zones, which is inconvenient and loss giving, and also for other reasons a higher concentration can be directly undesired.

At its outset, the invention is based on another airlaying technique than indicated above, viz. of the type disclosed in EP-B-0,032,772. This is a technique which, among experts, is recognised as highly characteristic for the present applicant. It is advantageous by a high production capacity and evenness of the formed web, but it has been noted that there are problems with respect to achieving a homogenous admixture of the absorbing powder in the fibre material as laid out on the production wire.

The technique in question is particularly relevant for the production of relatively large web widths, e.g. in the range of 50–300 cm, so for the production of narrower, absorbing pad products it is actual to cut the web into stripes, rendering such a production more economical than the forming of single webs with the required width or widths.

However, it is then critical to obtain a high degree of evenness of the SAP distribution across the width of the web, as the web stripes will otherwise be non-uniform.

The discussed technique is based on the air fluidized fibres being moved in an air flow across the forming wire inside a perforated, rotating drum pipe and back again through another, corresponding drum pipe, whereby this set of drum pipes constitutes a forming head, from which the fibres are brought out into a space, in or through which, as conventionally, an air flow is drawn downwardly by the action of a suction fan connected to a suction box beneath the foraminous wire. The flow of fibres thus leaving the drum pipes will have a certain movement component transversely of the wire direction, but since the fibre flow is guided across the wire in two opposite directions the resulting fibre web will still be built up with sufficient and uniform layer thickness along both of its side edges, With suitable adjustments this will hold true for the fibre material, but not therewith for the SAP material, which may be affected quite differently by the respective transverse and vertical air flows. In practice it has been found that with a simple admixture of the SAP into the fibre material, the powder is deposited on the wire with another distribution characteristic than that of the fibre material, whereby it is very difficult or impossible to adjust the distribution so as to achieve a perfect result, which is an evenly distributed fibre web with an even admixture of the SAP powder. One of them can be optimised, but then not the other.

On this background, with the different airlaying techniques it has been required to accept compromises owing to the fact that the relevant air flows do not affect the fibres and the powder in exactly the same manner.

With the invention it has been recognised that it is possible to change and improve this picture in arranging for an admixture of the powder at a middle stage of the fibre distribution, i.e. after an initiated distribution, but before it is finalised, when care is taken to introduce the powder separately over at least an essential part of the width of the web, just as in connection with the first mentioned method of applying a middle layer of the SAP material.

It is achieved hereby that the SAP powder will not be noticeably affected by the initial distribution influence on the fibre material, whereby the fibre distribution can be controlled for achieving a uniform distribution profile without special attention to the admixture of the SAP material, while the latter may take place with a compulsory broad distribution at such a late stage that the powder will still just have time to be fully mixed with the fibres-while these are under final delivery to the forming wire. It is ensured hereby that a real and current mixing of the powder into the fibre material will occur and that the admixture may be uniform all over the width of the web, There may of course be a certain range of compromise, in which the SAP material, all according to the detailed circumstances, nay be added sooner or later in the supply course of the fibres, and correspondingly the supply of the SAP can be more or less uniform over the web width, if a certain inhomogeneity is acceptable. By such lower quality requirements, the invention will still be advantageously usable, as the SAP supply is then particularly easy to control.

Normally, for obtaining the better qualities it should be chosen to add the SAP at such a late stage of the process that there is not much turbulence left in the air which brings the fibres towards the web, and it may be preferable, therefore, to supply the SAP material through means operable to actively spread the SAP, such that the materials may still be intensively mixed together just before the delivery to the forming wire.

By the production of narrow webs it is known to add the SAP material by injection into the fibre space in the forming head, see e.g. U.S. Pat. No. 4,927,582 and EP-A-520,798, but it such connections the conditions are less critical, because the material supply is, beforehand, distributed over a noticeable part of the width of the web, and also, it will be less important whether a reduced SAP admixing occurs along the side edges of the single web pieces.

The problem considered will occur by all broad web laying techniques, so the invention is not limited to the discussed special laying technique for the fibre web.

In the following the invention is described in more detail with reference to the drawing, in which.

Figure 1:
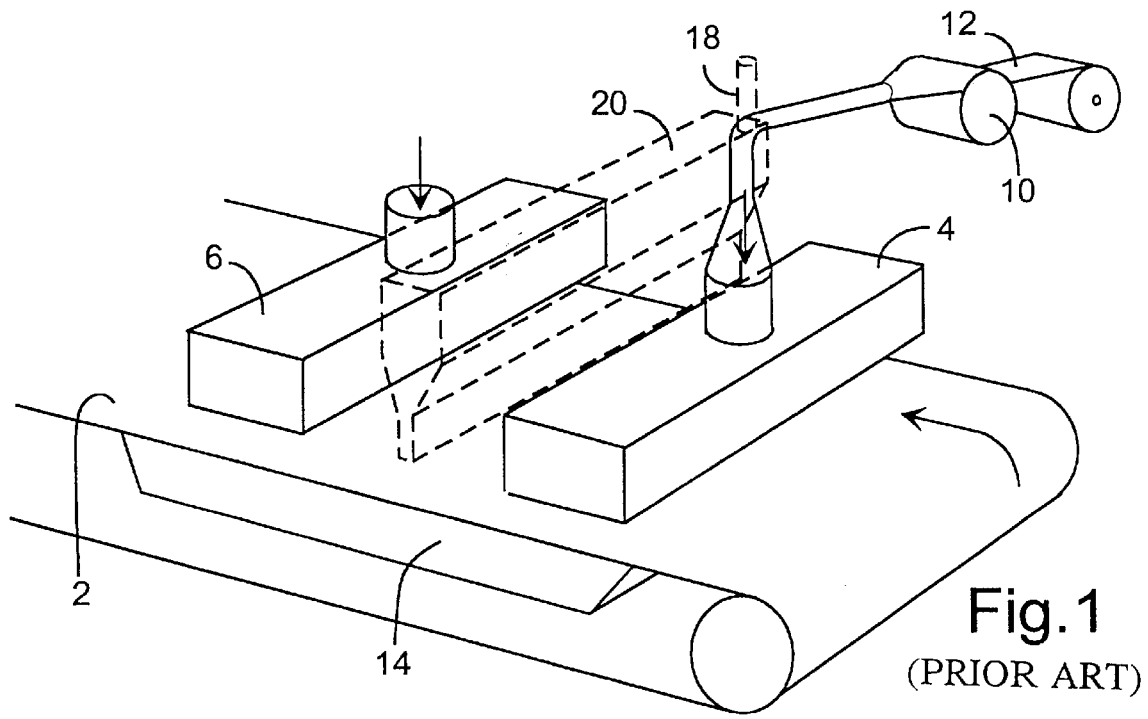
FIG. 1 is a perspective view of a dry forming system with means for supplying SAP material conventionally.
Figure 2:
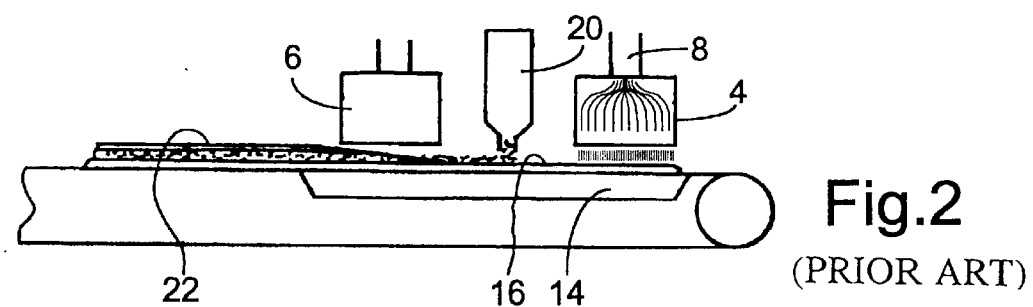
FIG. 2 is a longitudinal sectional view thereof.

FIGS. 1 and 2 show a dry forming system very schematically. The system comprises a perforated forming wire 2 with forming head equipment mounted thereabove, here shown as two forming heads 4 and 6, which each receives a flow of a air fluidized fibre material through supply channels 8. It is shown that this material is received from a hammer mill 10, which is currently fed with a web 12 of pulp material that is defibrated in the hammer mill. Underneath the wire 2 a suction box 14 in mounted, from which air is sucked down through the wire such that the fibre material as distributed over the width of the wire inside the forming heads is sucked down for formation of a more or less even, light web layer 16 on the wire.

As mentioned, it is possible to obtain an incorporation of a super absorbing powder (SAP) in the final product by supplying the powder to an air/fibre flow fed to a forming head, e.g. by supplying it through a pipe 18 as shown in dotted lines in FIG. 1, or by using a powder dispenser 20, from which the powder is sprinkled down over the entire width of the web 16 delivered frown the forming head 4, whereafter the other forming head 6 will lay out a top web 22 on the powder layer. However, it is these two methods which are sought to be improved by the present invention.

Figure 3:
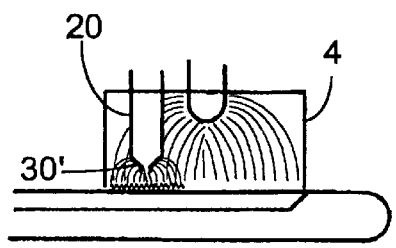
FIGS. 3 and 4 are corresponding views of two systems according to the invention.
Figure 5:
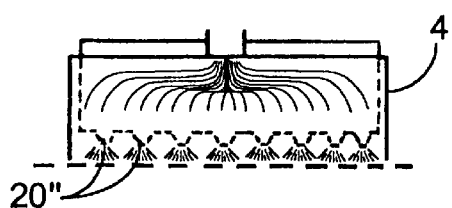
FIGS. 5 and 6 are cross sectional views thereof.

FIG. 3 indicates a system solution according to the invention. Inside the applied forming head 4 there is mounted a powder dispenser 20 extending almost or entirely over the width of the web and having its lower outlet end 20 located inside the proper fibre distribution room, spaced above the wire 2. At such a place there nay be sufficient air turbulence for the powder to be spread out so as to well mixed with the fibre material which—still in air fluidized condition is under motion with a component down towards the wire 2, but according to the invention it is a preferred option to use a powder dispenser modified such that the dispenser, by itself or by separate means arranged at the mouthing 20, effects an active spreading of the powder. If such a spreading is effected in both the longitudinal and the transverse direction of the web, then the dispenser may, as shown in FIG. 5, be shaped with a transverse row of mutually spaced outlets 20", but it is preferred to use an unbroken outlet slot 20 in combination with means for spreading the powder in the length direction of the web, as also mentioned below.

Figure 4:
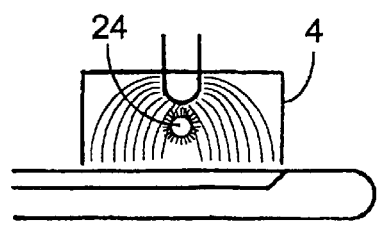

In the embodiment shown in principle in FIG. 4 a special powder distributor is used, viz. a transverse, perforated tube 24 extending across the forming head 4 and housing a conveyor for powder supplied from one end of the tube, e.g. a worm conveyor. Of course, even with this design it will be possible to use means for active spreading of the SAP powder, but it will not necessarily be required. In FIG. 4 it is indicated that the powder is introduced at a slightly higher level than in FIG. 3, i.e. in an area with higher turbulence, whereby it is less important to effect active powder spreading.

Figure 6:
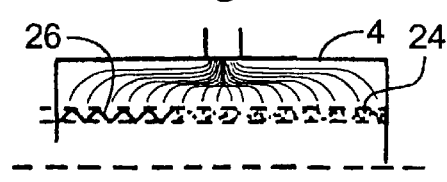

In FIG. 6, the transverse perforated tube 24 is seen from a long side of the forming head 4, with the said worm conveyor indicated at 26.

Figure 7:
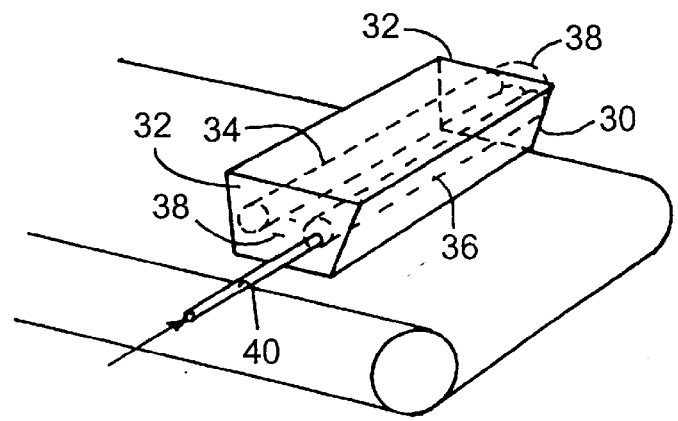
FIG. 7 is a perspective view of a preferred dry forming system.

The tore detailed experiments with the invention have been made in a dry forming system of the "Dan-Web" type which, e.g. according to EP-B-0,032,772, is characteristic in that the forming head 4, as shown in FIG. 7, comprises an outer box 30 with opposed narrow gable portions 32, between which there is arranged two parallel, perforated drum pipes 34 and 36 which at their ends are mutually connected through pipe bendings 38 which, at one or both ends of the box 30, are connected with a supply pipe 40 corresponding to the supply pipe 8 from the hammer mill 10 in FIGS. 1–5.

Figure 8:
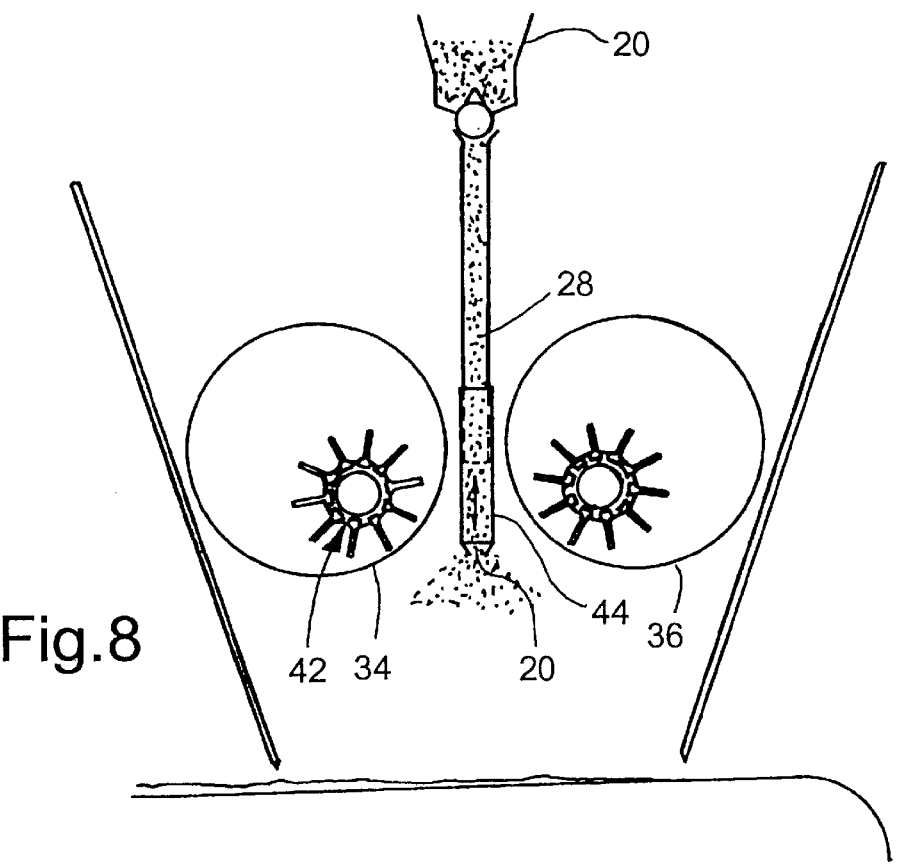
FIG. 8 is a sectional view thereof.
Figure 9:
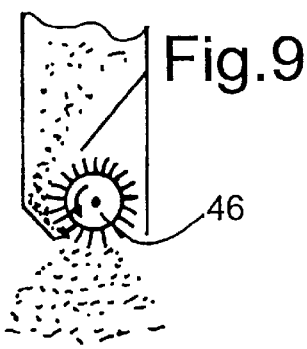
FIGS. 9–11 are sectional views illustrating different embodiments of the invention.

In operation, the fiber flow is thus supplied to one or both of the drum pipes 34,36 and is brought to circulate in the system 34,36,38. The drum pipes 34 and 36 are perforated 35 and are rotated, and as shown in FIG. 8 they are preferably provided with internal needle cylinders 42, which are rotated at high speed, whereby the fibres can be discharged from the drum pipes with high capacity and with high smoothness on the wire 2; a certain unevenness may occur by the transverse fiber movement in each of the drum pipes, but this will be remedied by an opposite unevenness by the movement through the other drum pipe. Thus, the two drum pipes is a pair of drums constituting a single forming head.

According to the invention and as shown in FIG. 8, a powder dispenser 20 with a downlet duct 28 may be mounted between the two drum pipes 34 and 36. As shown, the duct may be provided with a lower, vertically displaceable mouthing part 44, whereby the level of the outlet mouthing 20 may be adjusted.

Already hereby it is possible to supply the SAP powder in such a manner that it can be effectively mixed with the fibres by the existing turbulence, before the fibres are deposited on the wire 2, but according to the invention it is still preferable to make use of means for actively spreading the powder from the outlet mouthing 20

Thus, as shown in FIG. 5, a rotating brush cylinder 46 may be mounted along the mouthing 20, for spreading the powder.

Figure 10:
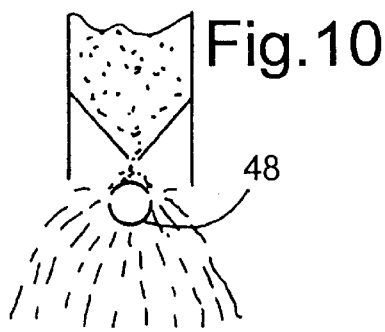

Another possibility is shown in FIG. 10, where a perforated compressed air pipe 48 is mounted beneath the outlet slot of the powder dispenser in order to spread the powder in the transverse direction of this pipe and thus to produce a good admixing of the powder into the fibre material before the final downlet onto the wire 2.

Figure 11:
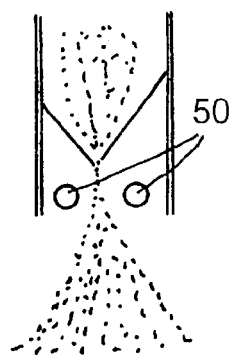

In FIG. 11 it is shown that a similar result may be obtained by means of a pair of rod electrodes 50 mounted beneath the mouthing 20, again for spreading the powder.

Figure 12:
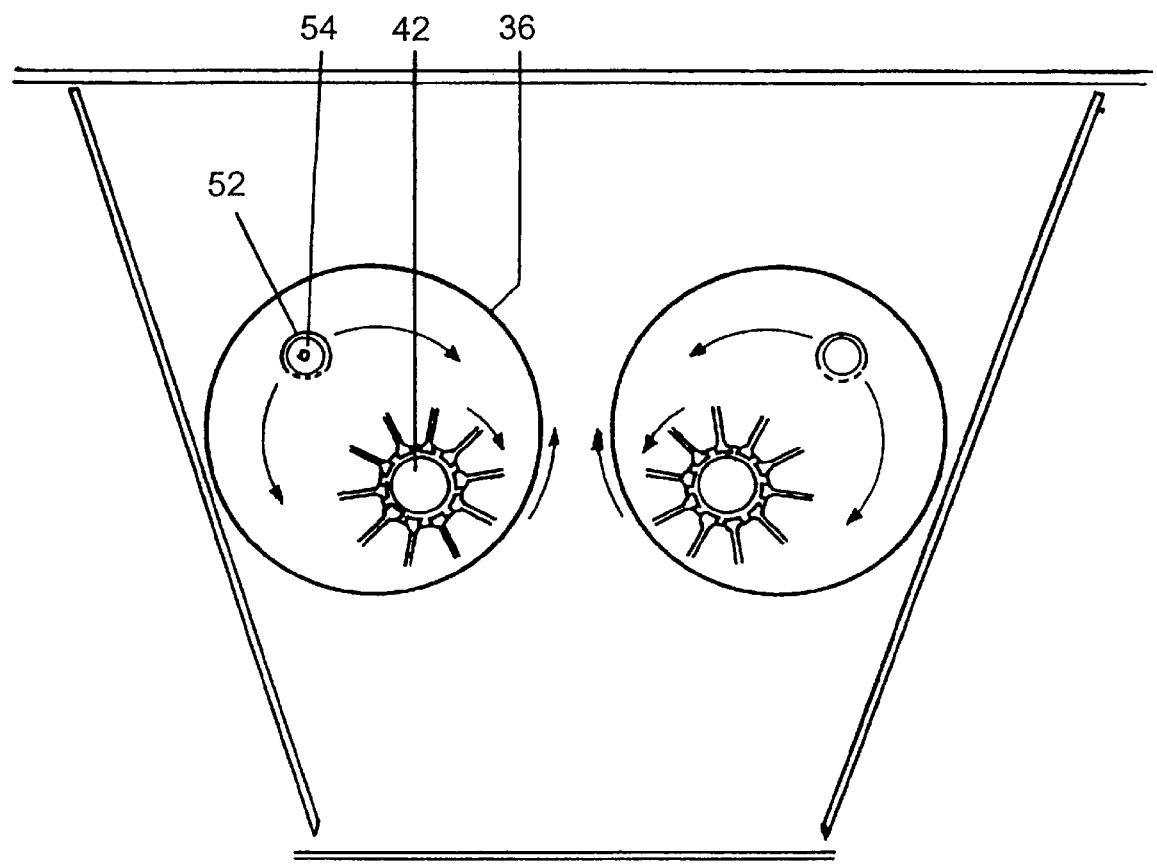
FIGS. 12 and 13 are sectional views illustrating still another embodiment.
Figure 13:
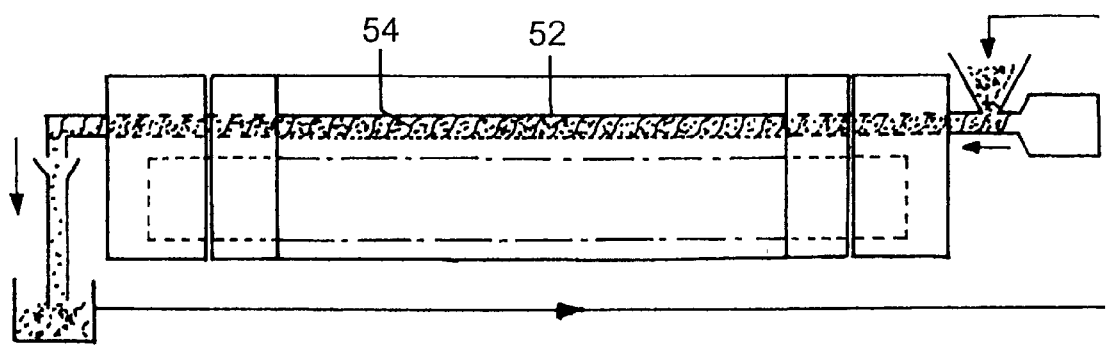

FIGS. 12 and 13 show a modified embodiment of the invention in a system of the discussed type. Here, there is mounted internally in one or preferably both of the drum pipes an axial parallel dispenser pipe 52, which, as indicated in FIG. 12, may be adjustably mounted. This pipe is perforated at its lower side, and it contains a worm conveyor 54 which, from a non-illustrated supply, is operable to bring the SAP powder through the pipe such that the powder is let out through the perforated pipe bottom with a suitable capacity. It should be ensured that there is sufficient powder all over the length of the pipe, also at the end opposite to the infeed end, and since it may also be desired to adjust the capacity of the system by changing the rotation speed of the worm conveyor the system should preferably be dimensioned such that even at low capacity there is conveyed a surplus of powder, whereby the final surplus may be collected at the outlet end of the pipe.

Instead of a worm conveyor 52, it will be possible to use an entrainment chain which, if desired, may run forwardly through the pipe in one of the pipe drams and return through the pipe in the other pipe drum.

We claim:

1. A method of manufacturing airlaid paper webs with a width of more than 30 cm and with a content of a superabsorbing powder material, so-called SAP, whereby the paper web is formed on a foraminous wire in guiding down against this wire an air fluidized flow of cellulose fibres from an overlying distributor unit, supported by an active suction effect at the underside of the wire, the thus formed fibre web on the moved wire being subsequently stabilized by addition of a binder from outside or by actuation of an initially admixed binding agent, typically by heating for actuation of admixed heat actuated binding fibres after the addition of the absorbing powder material to the web, characterized in that the absorbing powder material is added in an intermediate stage of the fibre distribution, the powder supply being arranged such that the powder is distributed in a compulsory manner throughout the entire width of the initially formed web or over partial width sections thereof, whereafter the powder is fully distributed by the action of the air flow operating to effect the final distribution of the fibre material on the forming wire.

2. A method according to claim 1, whereby there is used a fibre distributor of the type comprising two or more forming heads arranged successively in the moving direction of the wire, inside a common forming box, characterized in that the addition of the absorbing powder is effected by conducting the powder down through a flat duct or a number of downwardly projecting pipes in the intermediate space between two such forming heads.

3. A method according to claim 1, characterized in that the absorbing powder is let down through a slot forming channel, at the lower delivery end of which there is arranged means for actively producing a controlled spreading of the powder.

4. A method according to claim 1, characterized in that the absorbing powder is supplied via a perforated tube extending across the web length inside the forming space, the powder being conveyed through the tube by means of a conveyor, from one end thereof, such that despite the letout of the powder through the perforations there will occur a powder let-through for recirculation from the other end of the pipe.

5. A method according to claim 4, in which there is used for the laying out of the fibres a forming head of the type having two juxtaposed, perforated pipe drums located in a common forming box, characterizied in that the absorbing powder is supplied internally in such a pipe drum.

6. A method according to claim 1, wherein said intermediate stage of the fibre distribution when the absorbing powder material is added, is after the initial forming of the air fluidized fibre flow and prior to the final depositing of the fibres on the forming wire.

7. A system for producing an airlaid paper web by the method according to claim 1, with a forming head operable to spread out an air fluidized fibre current over a moved-forming wire with a web width of at least 30 cm, characterized in that the forming head is provided with internal supply means for feeding powder to the area just above the forming zone, these means having outlet mouthing areas located with uniform distribution all over the width of the web.

* * * * *